United States Patent [19]

Tatsuno

[11] Patent Number: 4,801,205
[45] Date of Patent: Jan. 31, 1989

[54] PARTICLE SIZE MEASURING APPARATUS

[75] Inventor: Kyoichi Tatsuno, Yokohama, Japan

[73] Assignee: Kabushiki Kaisha Toshiba, Kawasaki, Japan

[21] Appl. No.: 739,283

[22] Filed: May 30, 1985

[30] Foreign Application Priority Data

Jun. 30, 1984 [JP] Japan .................. 59-135972
Jun. 30, 1984 [JP] Japan .................. 59-135978

[51] Int. Cl.$^4$ .................. G01B 11/08; G01N 15/02
[52] U.S. Cl. .................. 356/336; 356/343
[58] Field of Search .................. 356/336, 343, 338

[56] References Cited

U.S. PATENT DOCUMENTS

| 3,646,352 | 2/1972 | Bol et al. | 356/336 |
| 3,835,315 | 9/1974 | Gravitt . | |
| 3,869,208 | 3/1975 | Lorenz | 356/336 |
| 3,873,206 | 3/1975 | Wilcock | 356/336 |
| 4,173,415 | 11/1979 | Wyatt | 356/336 |
| 4,245,909 | 1/1981 | Loos | 356/336 |
| 4,264,206 | 4/1981 | Hattori | 356/343 |
| 4,475,816 | 10/1984 | Mooradian et al. | 356/338 |
| 4,497,577 | 2/1985 | Sato et al. | 356/343 |
| 4,538,915 | 9/1985 | Faulhaber | 356/431 |
| 4,565,446 | 1/1986 | Chu | 356/343 |

FOREIGN PATENT DOCUMENTS

| 0106684 | 10/1983 | European Pat. Off. . |
| 2204079 | 8/1973 | Fed. Rep. of Germany . |
| 3220785 | 1/1983 | Fed. Rep. of Germany . |
| 3315456 | 12/1984 | Fed. Rep. of Germany . |

OTHER PUBLICATIONS

AIAA Paper No. 76-69, A Laser Diagnostic Technique for the Measurement of Droplet and Particle Size Distribution, Swithenbank et al., 1976.
The 1st International Conference on Liquid Atomization and Spray Systems (Tokyo, Japan), a Light Scattering Technique For Determining Droplet Size Distributions in Two-Phase LIquid-Dominated Nozzle Jets, Alger et al., 1978.

Primary Examiner—Richard A. Rosenberger
Attorney, Agent, or Firm—Oblon, Fisher, Spivak, McClelland & Maier

[57] ABSTRACT

A particle size measuring apparatus irradiates a number of particles to be measured with a laser beam, measures a light intensity pattern scattered by the particles to be measured, and calculates a relative particle size distribution of the particles to be measured from the measured value obtained. The apparatus has a laser unit, a collimator lens for collimating a laser beam from the laser unit into a parallel laser beam and irradiating the particles to be measured with the parallel laser beam, an optical shield, interposed between the collimator lens and the particles to be measured, for shielding scattered light by the collimator lens and allowing passage of only parallel components of the laser beam, a detecting section consisting of a plurality of optical fibers arranged at an equal distance from a measurement region and at predetermined scattering angles and photodetectors connected thereto, and an arithmetic operating circuit for calculating a relative particle size distribution of the particles to be measured from the scattered light intensity pattern detected by the detecting section.

3 Claims, 6 Drawing Sheets

PARTICLE SIZE MEASURING APPARATUS

BACKGROUND OF THE INVENTION

The present invention relates to a particle size measuring apparatus for measuring the diameter of small particles or microparticles.

A particle size measuring apparatus is known which measures the particle size distribution of particles such as water droplets in a turbine or fuel droplets in a combustion apparatus. One of the particle size measuring methods is the forward scattering method.

The principle of the forward scattering method is as follows.

A parallel monochromatic light such as a laser beam is irradiated on a number of particles to be measured. The angular pattern of the scattered light intensity, which is named the scatted light intensity pattern, is measured. The scattered light intensity pattern $I(\theta)$ is inverted to the particle size distribution $n_r(D)$ by solving Eq. (1)

$$I(\theta) = \int i(D,\theta) n_r(D) dD, \quad (1)$$

where $i(D,\theta)$ is the light intensity scattered by a D diameter spherical particle and $\theta$ is scattering angle. Eq. (1) expresses that the scattered light intensity pattern is superpositions of the light intensity $i(D,\theta)$ scattered by a D diameter particle. The light intensity $i(D,\theta)$ scattered by a spherical particle can be calculated by the Mie theory. Therefore, Eq. (1) can be solved. The present inventor previously proposed an apparatus for measuring particle size distribution $n_r(D)$ of a number of particles to be measured as stated in U.S. patent application No. 541,023, filed on Oct. 12, 1983, entitled "A Particle Diameter Measuring Device" now U.S. Pat. No. 4,595,291, issued June 17, 1986. In this apparatus, a laser radiated from a laser unit is converted into a parallel laser beam with an adequate diameter through an optical system such as a collimator lens. The parallel beam is irradiated on a number of particles to be measured. Scattered light intensities $I_1$ to $I_n$ at respective scattering angles $\theta_1$ to $\theta_n$ are measured by photodetectors arranged at the respective scattering angles $\theta_1$ to $\theta_n$ and at equal distances from the center of a measurement area. Measured light intensity $I(\theta)$ ($I_1, I_2, \ldots, I_n$) is inverted to particle size distribution by the Logarithmic Constrained Inversion Method or the Logarithmic Distribution Function Approximation Method using Eq. (1).

In this apparatus, the laser beam from the laser unit is scattered by a collimator lens. The light scattered by the collimator lens causes background noise when the scattered light intensity pattern for a number of particles is measured. When a number of particles to be measured is small, this background noise becomes significant problem and the S/N ratio of the measured light intensity pattern is small.

In the above-mentioned apparatus, the scattered light intensity pattern is obtained as a relative value, and the particle size distribution inverted is also a relative value and can only be obtained, for example, as a particle size distribution density function.

SUMMARY OF THE INVENTION

An object of the present invention is to provide a particle size measuring apparatus which can measure the scattered light intensity pattern of a number of particles to be measured with a high S/N ratio without background noise generated by a collimator lens.

Another object of the present invention is to provide a particle size measuring apparatus which can obtain an absolute particle size distribution, i.e., a particle size distribution expressed in terms of the number of particles.

According to one aspect of this invention, there is provided a particle size measuring apparatus in which an aperture for shutting off the light scattered by the collimator lens is arranged between particles to be measured and the collimator lens.

According to another aspect of this invention, there is provided a particle size measuring apparatus in which conversion coefficients from the relative value of a scattered light intensity pattern to the absolute value of it, where the absolute value means the value expressed as light energy (W), are prestored for each scattering angle. The conversion coefficients are obtained as the ratio of the calculated value and the measured value of the light intensity scattered by the particles with a known particle size distribution and particle density (numbers/cm$^3$). The particle density of particles to be measured can be determined from the absolute value of the scattered light intensity pattern. The absolute particle size distribution is determined as the product of the particle density and the relative particle size distribution.

DETAILED DESCRIPTION OF THE PREFERRED EMBODIMENTS

Figure 1:
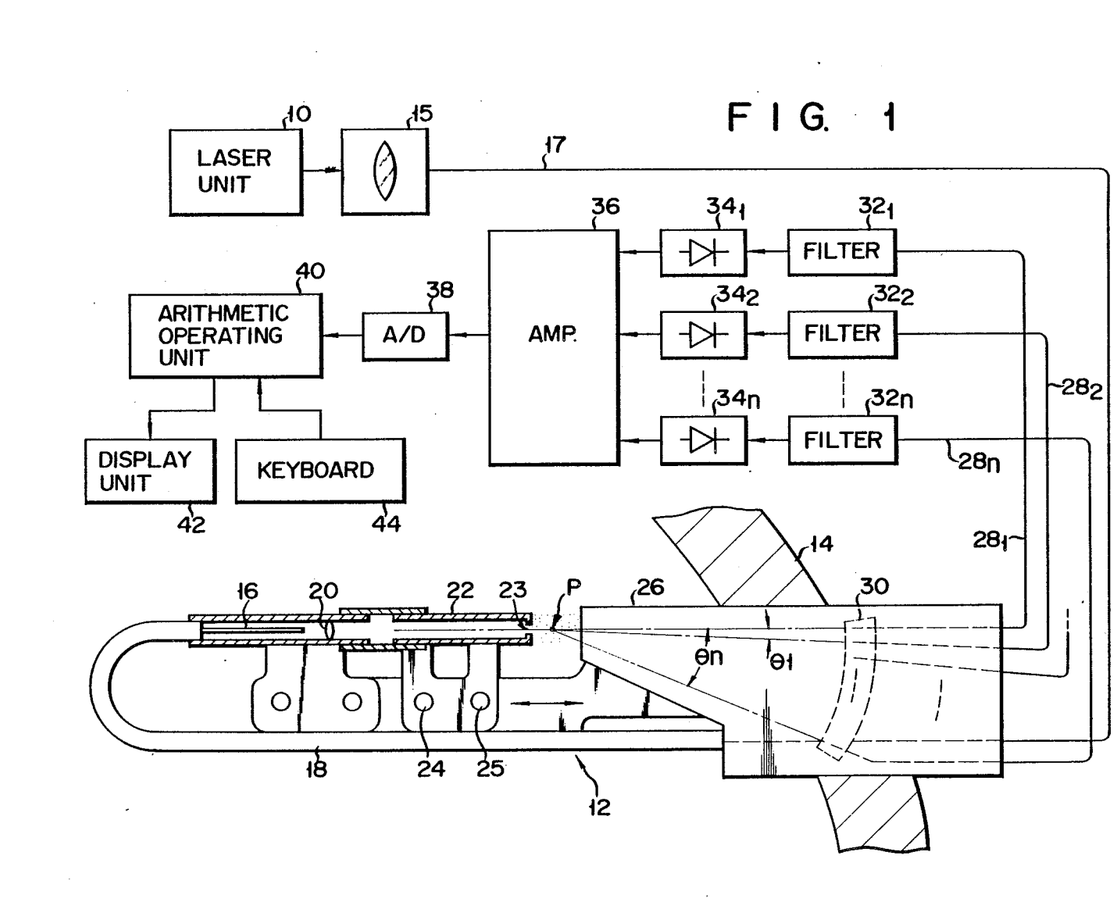
FIG. 1 is a schematic diagram of a particle size measuring apparatus according to a first embodiment of the present invention.

A particle size measuring apparatus according to a first embodiment of the present invention will be described on referring to the drawings. FIG. 1 is a schematic diagram of the particle size measuring apparatus for measuring the size of water droplets in a turbine according to the first embodiment. The apparatus of this embodiment comprises a laser unit (e.g., an Ar-ion laser unit or an He-Ne laser unit) 10, a measuring probe 12 for radiating a laser beam oscillated from the unit 10 onto a number of particles (droplets) to be measured in a scattering region P and for receiving light scattered by the particles, and an electrical circuit for inverting the particle size distribution from the scattered light intensity measured by measuring probe 12. The probe 12 is inserted into a turbine casing 14 for measuring water droplets in a turbine, as shown in FIG. 1. Output light from the laser unit 10 is focused and is incident on one end of an optical fiber 17 by a laser/fiber connector 15 comprising a lens. The tip of the probe 12 comprises a U-shaped pipe 18 for guiding the optical fiber 16 to near the scattering zone P, a collimator lens 20 for converting the incident laser beam into a parallel laser beam with a predetermined diameter, and a cylindrical light-shield 22 which has an aperture 23 at the center of the end. The diameter of the aperture 23 is set to be slightly larger than that of the parallel laser beam radiated from the collimator lens 20. The light-shield 22 can slide in the direction of the arrow by loosening screws 24 and 25 so as to adjust the distance between the lens 20 and the aperture 23 of the member 2. The light-receiving part of the probe 12 comprises a light-receiving tube 26 in which an optical fiber holder 30 is arranged so as to hold the distal ends of optical fibers $28_1, 28_2, \ldots, 28_n$ at an equal distance from the center P of the scattering zone and at scattering angles $\theta_1, \theta_2, \ldots, \theta_n$, respectively.

The fibers $28_1, 28_2, \ldots, 28_n$ are connected to the photodetectors $34_1, 34_2, \ldots, 34_n$, (e.g., photodiodes) through interference filters $32_1, 32_2, \ldots, 32_n$, respectively. Outputs from the photodetectors $34_1, 34_2, \ldots, 34_n$ are fed to an arithmetic operating unit 40 through an amplifier 36 and an A/D converter 38. A display unit 42 for displaying results and a keyboard 44 for data input are also connected to the arithmetic operating unit 40.

Figure 2:
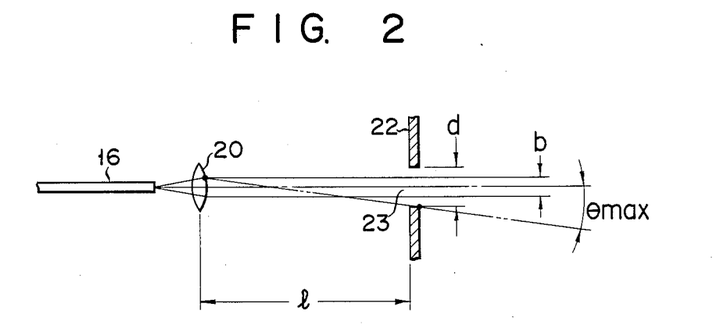
FIG. 2 is a graphical representation for explaining the principle of the first embodiment of the present invention.

The operations the particle size measuring apparatus according to the first embodiment will be described below. A laser beam oscillated from the laser unit 10 is led to the probe 12 through the lens 15 and the fiber 17 and a parallel laser beam with a predetermined diameter is formed by the collimator lens 20. The laser beam passed through the lens 20 is partially scattered by the collimator lens 20. According to this embodiment, the laser beam radiated from the lens 20 is irradiated onto a number of particles to be measured in the scattering zone through the aperture 23 of the light-shield 22. Therefore, most of the scattered light is shielded by the light-shield 22. As a result, the laser beam irradiated onto the particles to be measured through the aperture 23 is substantially a parallel laser beam. A shown in FIG. 2, a maximum scattering angle $\theta_{max}$ of scattered light by the collimator lens after passing through the aperture 23 is given by:

$$\theta_{max} = \tan^{-1}\{(b+d)/2l\} \quad (2)$$

where b is the diameter of a parallel laser beam radiated from the collimator lens 20, d is the diameter of the aperture 23, and l is the distance between the lens 20 and the aperture 23 at the distal end of the light-shield 22. In order to suppress the noise by the scattered light (i.e., to minimize $\theta_{max}$), the diameter d of the aperture 23 is set to be small and is preferably set to equal the diameter b, or the distance l between the lens 20 and the aperture 23 is set to be long.

In this manner, since light scattered by the collimator lens can be shielded, only scattered light by the particles to be measured is incident on the optical fibers $28_1, 28_2, \ldots, 28_n$ and scattered light intensities $I_1, I_2, \ldots, I_n$ at the scattering angles $\theta_1, \theta_2, \ldots, \theta_n$ are measured with a high S/N ratio. Particle size distribution $n_r(D)$ (relative value) is inverted by Eq. (1) from the measured scattered light intensity pattern $I(\theta)=(I_1, I_2, \ldots, I_n)$ by the Logarithmic Constrained Inversion Method or the Logarithmic Distribution Function Approximation Method.

Figure 3:
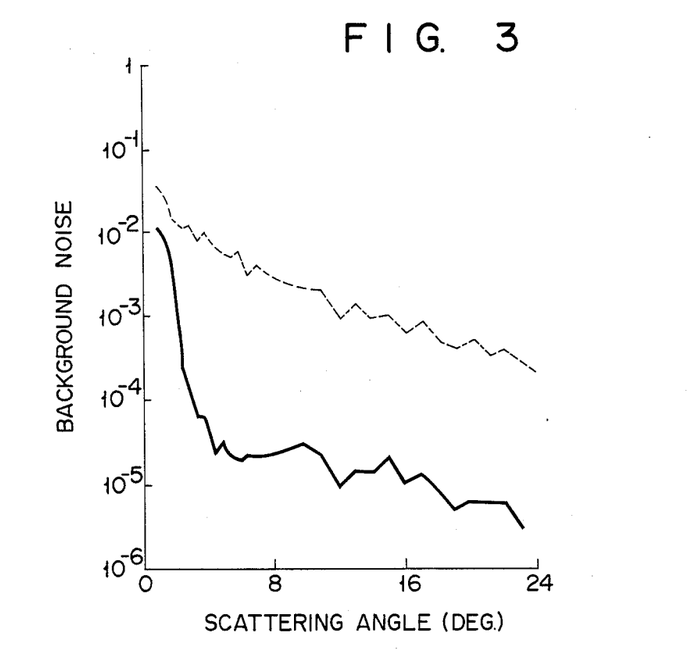
FIG. 3 shows the effect of the first embodiment by comparing the background noise of the present apparatus with that of a conventional one.

According to the first embodiment, the light-shield 22 with the aperture 23 is inserted between the collimator lens 20 and the particles to be measured so as to shut off scattered light by the collimator lens and to allow only the parallel laser beam to pass. Therefore, light scattered by the collimator lens 20 will not cause background noise and will not adversely affect the measurement of the particle size distribution. FIG. 3 shows the measurements of background noises obtained in the apparatus of this embodiment and a conventional apparatus. The solid line shows the background noise in the apparatus of the embodiment wherein b=1.2 mm and d=1.5 mm. The broken line shows that in the conventional apparatus. It is evident that the background noise is reduced in this embodiment to 1/100 that in the conventional apparatus.

In the above embodiment, the light-shield has a cylindrical shape. However, the shape of the light-shield is not limited to this. It is only required that an optical light-shield which have an aperture with slightly larger diameter than that of the laser beam is arranged at a predetermined distance from a collimator lens.

Figure 4:
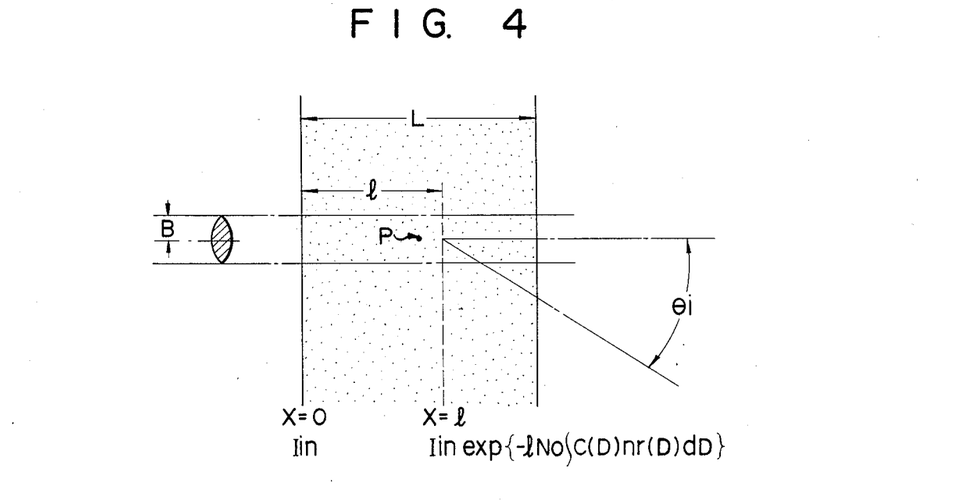
FIG. 4 is a graphical representation for explaining the principle of a particle size measuring apparatus according to a second embodiment of the present invention.

A second embodiment of the present invention will be described below. According to the first embodiment, background noise caused by light scattered by a collimator lens is reduced in order to make measurement with a high S/N ratio. The objective of the second embodiment is to measure an absolute size diameter distribution, i.e., a distribution expressed in terms of the number of particles which diameters are within the range between D and D+ΔD. In the second embodiment, the absolute value of the particle size distribution is obtained in accordance with the following steps. As shown in FIG. 4, when a particles to be measured with a particle density $N_o$ in a scattering zone with optical path length L is irradiated with a laser beam with radius B, the scattered light intensity pattern $I(\theta)$ considering the attenuation of incident light along the optical path is given by:

$$I(\theta) = \int_0^L \left[ I_{in} \exp\left\{ -xN \int_o^c (D)n_r(D)dD \right\} \int_x^i (D,\theta)\pi B^2 N_o n_r(D)dD \right] dx \quad (3)$$

wherein $I_{in}$ is the incident light intensity and c(D) is the scattering cross section.

Substituting X and A given by:

$$X = \int c(D)n_r(D)dD \quad (4)$$

$$A = I_{in}\pi B^2 \quad (5)$$

Eq. (3) can be rewritten as:

$$I(\theta) = A \left\{ \int_0^L \exp(-xN_oX)dx \right\} \tag{6}$$

$$\int_x^i (D,\theta)n_r(D)dD$$

Integration for x in Eq. (6) yields:

$$I(\theta) = (1/X) \times [A\{1-\exp(-LN_oX)\}] \times \int i(D,\theta)n_r(D)dD \tag{7}$$

Scattering cross section c(D) is a known value and scattered light intensity $i(D,\theta)$ by one particle is obtained by the Mie scattering theory. Relative particle size distribution $n_r(D)$ can be obtained by Eq. (1) from the relative value $I_m(\theta)$ of scattered light intensity pattern. Therefore, if absolute value $I(\theta)$ of the scattered light intensity pattern, i.e., the scattered light intensity pattern represented by light energy (W) can be obtained by any method, the particle density $N_o$ of the particles to be measured can be determined by Eq. (7).

Absolute value $I(\theta)$ of the scattered light intensity pattern is obtained as follows. Particles with known diameter R and particle density $N_o$ are irradiated with a laser beam and its scattered light intensity pattern $I_{pm}(\theta)$ is measured. If the measurement system has a total conversion efficiency $\eta(\theta)$ from the light energy to electric voltage, the measurement $I_{pm}(\theta)$ is given by:

$$I_{pm}(\theta) = \eta(\theta) \times I_p(\theta) \tag{8}$$

where $I_p(\theta)$ is the absolute value (theoretical value) which is calculated based on the scattering theory. In the measuring apparatus shown in FIG. 1, when light-receiving efficiency of the optical fiber $28_i$ arranged at the scattering angle $\theta_i$ is represented by $nR_i$, transmittance of the optical fiber $28_i$ is represented by $\eta P_i$, the conversion efficiency of the photodiode $34_i$ is represented by $\eta T_i$ and the gain of the amplifier $36_i$ is represented by $\eta A_i$, total conversion efficiency $\eta(\theta)_i$ of the measurement system is given by:

$$\eta(\theta_i) = \eta R_i \times \eta P_i \times \eta T_i \times \eta A_i \tag{9}$$

The diameter D and particle density $N_o$ of the particles for calibration are known. Therefore, when a laser beam has unit area and unit energy density, i.e., when $A=1$ is substituted in Eq. (5), theoretical value $I_p(\theta_i)$ of the scattered light intensity pattern at the scattering angle $\theta_i$ can be calculated by Eq. (7). Based on the theoretical value $I_p(\theta_i)$ and measured value $I_{pm}(\theta_i)$, a conversion coefficient $T(\theta_i)$ between the absolute and measured values of the scattered light intensity pattern is given by:

$$\begin{aligned} T(\theta_i) &= 1/\eta(\theta_i) \\ &= I_p(\theta_i)/I_{pm}(\theta_i) \end{aligned} \tag{10}$$

The conversion coefficients for all the scattering angles are calculated in this manner and are given as $T(\theta)$. When the conversion coefficients $T(\theta)$ are determined in this manner, the absolute value $I(\theta)$ of the scattered light intensity pattern is determined from the measured value $I_m(\theta)$ of the scattering light intensity pattern by particles to be measured with unknown diameter D and particle density $N_o$ as follows:

$$I(\theta) = T(\theta) \times I_m(\theta) \tag{11}$$

When the absolute value $I(\theta)$ of the scattering light intensity pattern is determined, absolute value n(D) of the particle size distribution of particles to be measured is determined in the following manner. When the conversion coefficient $T(\theta)$ is calculated under the condition $A=1$, if $$C_{scat} = (1/X) \times \{1 - \exp(-LN_oX)\} \tag{12}$$

Eq. (7) can be rewritten as follows:

$$I(\theta) = C_{scat} \int i(D,\theta)n_r(D)dD \tag{13}$$

where $C_{scat}$ is expressed by Eq. (12).

From Eq. (13), $C_{scat}$ can be rewritten as follows:

$$C_{scat} = I(\theta)/\int i(D,\theta)n_r(D)dD \tag{14}$$

$C_{scat}$ can be obtained by substituting the absolute value $I(\theta)$ and the relative particle size distribution to Eq. (14). The relative particle size distribution $n_r(\theta)$ is calculated from the measured value $I_m(\theta)$ by the conventional method and the scattered light intensity $i(D,\theta)$ for each particle is calculated theoretically. When $C_{scat}$ is obtained, the particle density $N_o$ of the particles to be measured can be determined by the following equation which is solved Eq. (12) for $N_o$:

$$N_o = (-1/LX) \times \ln(1 - C_{scat}X) \tag{15}$$

Thus, the absolute distribution n(D) is given by:

$$n(D) = N_o \times n_r(D) \tag{16}$$

According to the procedure as described above, in the second embodiment, a conversion coefficient is determined as the ratio of the theoretical value to the measured value of the scattered light intensity pattern by particles with known diameter and known particle density and the conversion coefficients are prestored in a conversion table. The measured value of the scattered light intensity pattern obtained by particles to be measured is converted into the absolute value of the scattered light intensity pattern using the conversion coefficient in the conversion table, thereby obtaining the absolute value of the scattering light intensity distribution. The particle density of the particles to be measured is determined from this absolute value, and the absolute particle diameter distribution is calculated from the particle density and the relative particle diameter distribution of the particles to be measured.

Figure 5:
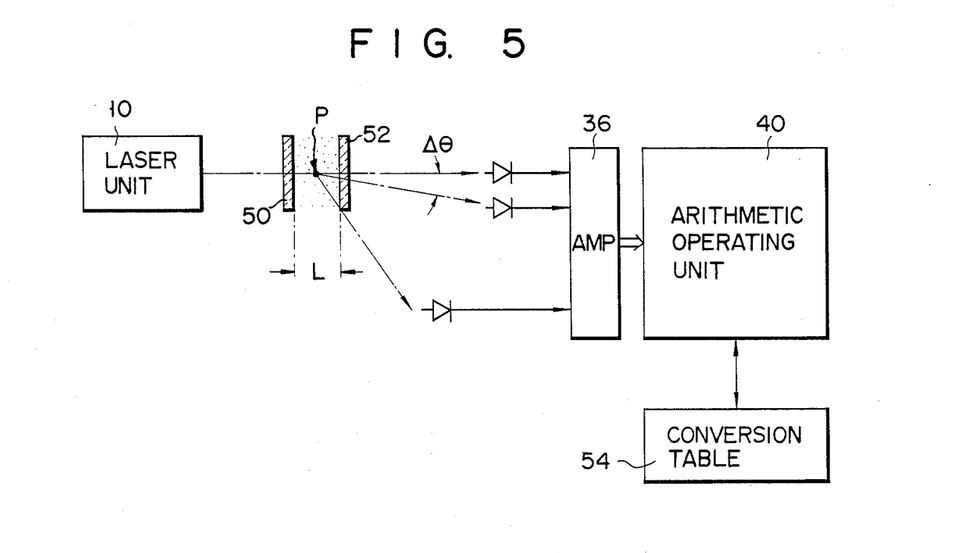
FIG. 5 is a schematic diagram showing a main part of the apparatus according to the second embodiment.

FIG. 5 shows the schematic configuration of a particle diameter measuring apparatus according to a second embodiment of the present invention. The configuration of the second embodiment is basically the same as that of the first embodiment except that in the second embodiment a scattering zone is limited by a pair of transparent material opposed at a predetermined interval L, e.g., glass plates 50 and 52, and that a conversion table 54 is connected to an arithmetic operating unit 40. The conversion table 54 comprises a memory unit and stores conversion coefficients $T(\theta)$ determined in the following manner.

First, particles with known particle diameter D and particle density $N_o$ is prepared for calibration. Such particles may be polystyrene particles, glass particles, and the like. In this embodiment, polystyrene particles are used. The weight of polystyrene particles and that of water are accurately measured with an electronic balance or the like, and they are mixed together. When the weight of the polystyrene particles is represented by $W_p$, the density (weight density) of polystyrene particles is represented by $\alpha_p$, the weight of water is represented by $W_w$ and the density (weight density) of water is represented by $\alpha_w$, particle density (number density) $n_p$ of the mixed suspension is given by:

$$n_p = \{(W_p/\alpha_p)/4\pi r p^3/3\}\{\times 1/\{W_p/\alpha_p)+(W_w/\alpha_w)\} \quad (17)$$

where $r_p$ is the radius of the polystyrene particles.

The suspension of the polystyrene particles in water is placed in the scattering zone P and the laser unit 10 is driven to irradiate the suspension with a laser beam. Light scattered by the polystyrene particles is led to the photodiode $34_i$ through the light-receiving fiber $28_i$ at the scattering angle $\theta_i$ ($i = 1, 2, \ldots, n$). A detected signal from the photodiode $34_i$ is fed to the arithmetic operating unit 40. In this manner, a measured value $I_{pm}(\theta)$ of the scattered light intensity pattern is obtained. Since diameter D and density $n_p$ of the polystyrene particles are known, the absolute value $I(\theta)$ of the scattered light intensity pattern is calculated by Eq. (3) in accordance with the scattering theory. The conversion coefficient $T(\theta_i)$ of the measured value $I_{pm}(\theta)$ and the absolute value $I(\theta)$ for each scattering angle $\theta_i$ can be calculated by:

$$T(\theta_i) = I_p(\theta_i)/I_{pm}(\theta_i) \quad (18)$$

The conversion coefficients $T(\theta)$ calculated are stored in the conversion table 54.

Subsequently, particles to be measured, which have unknown diameter D and particle density $N_o$ and for which the absolute particle size distribution must be determined, is arranged in the scattering zone P. Then, the laser unit 10 is driven to irradiate the particles with a laser beam of the same energy and beam diameter as those during the measurement for $I_{pm}$. As a result, the measured value $I_m(\theta)$ of the scattered light intensity pattern by the particles to be measured is obtained.

Figure 6:
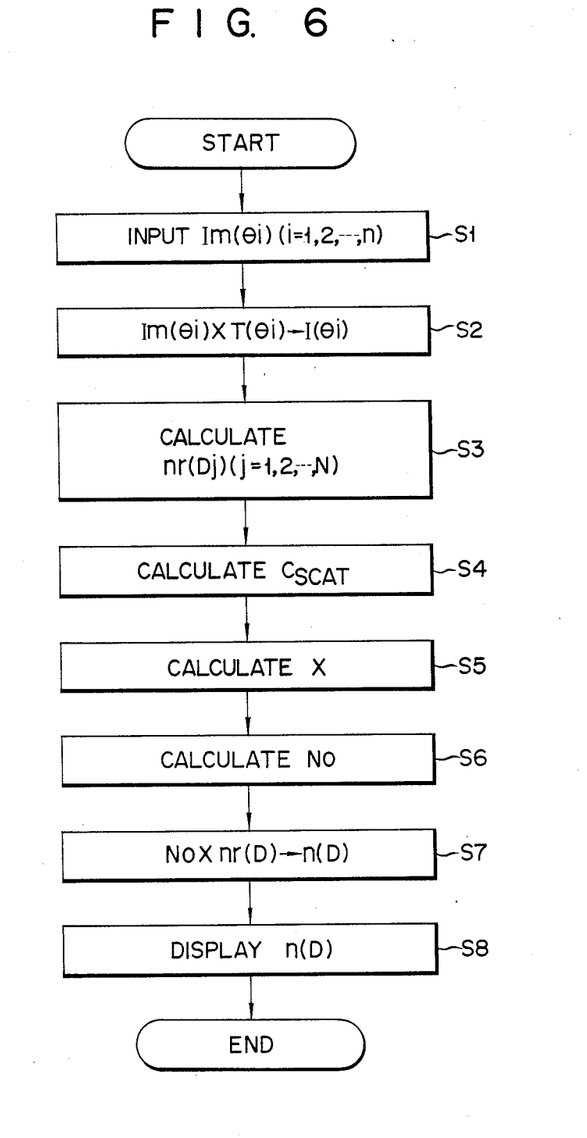
FIG. 6 is a flow chart for explaining the operations of the apparatus according to the second embodiment.

The arithmetic operating unit 40 calculates the absolute particle size distribution from the measured value $I_m(\theta)$ of the scattered light intensity pattern in accordance with the flow chart shown in FIG. 6. When measured value $I_m(\theta_i)$ ($i=1, 2, \ldots, n$) of the scattered light intensity distribution is entered in step S1, the conversion coefficient $T(\theta_i)$ is read out from the conversion table 54 and the measured value $I_m(\theta_i)$ is converted into the absolute value $I(\theta_i)$ by Eq. (11) in step S2. In step S3, the relative particle size distribution $n_r(D)$ is calculated from the absolute value $I(\theta_i)$ in accordance with Eq. (1). The relative particle size distribution $n_r(D)$ can be calculated by the Logarithmic Constrained Inversion Method or the Logarithmic Distribution Function Approximation Method. A detailed description of this calculation will be given later. After the relative particle size distribution $n_r(D)$ is calculated in this manner, the absolute particle diameter distribution n(D) is calculated in the following manner. In step S4, $C_{scat}$ is calculated by Eq. (14). In step S5, X is calculated by Eq. (4). In step S6, $N_o$ is calculated by Eq. (15). In step S7, n(D) is calculated by Eq. (16). In step S8, the absolute particle size distribution n(D) is displayed at the display unit 42.

Figure 7:
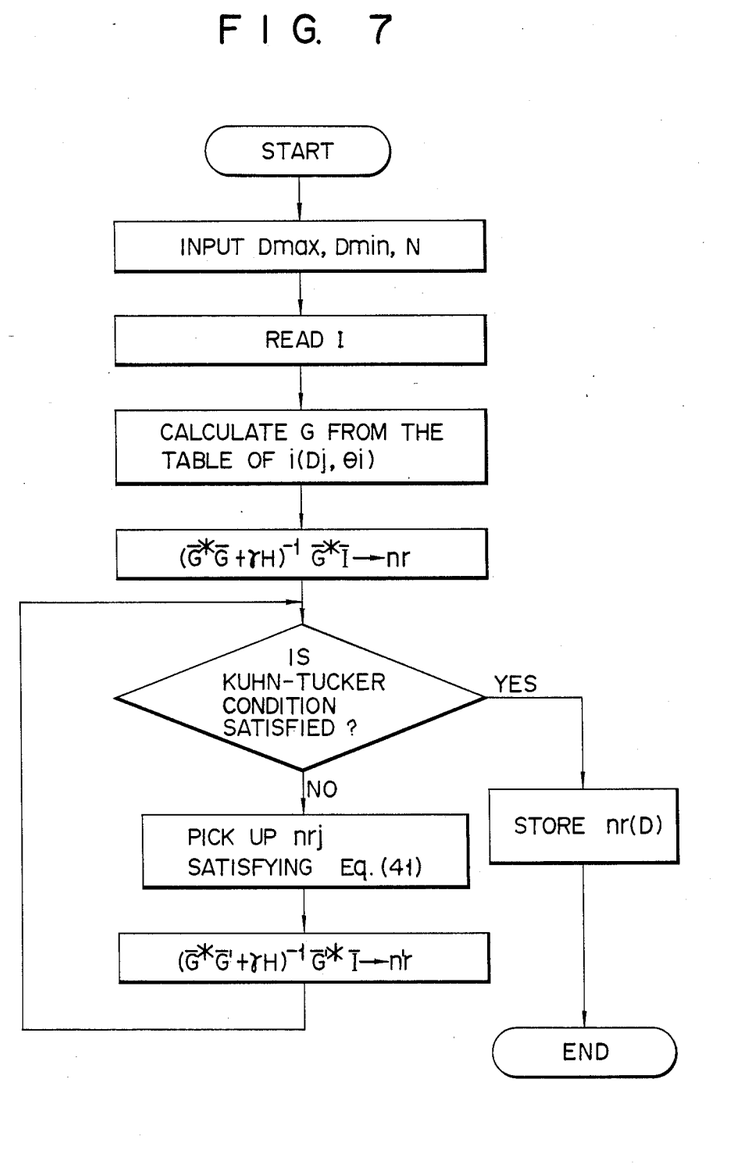
FIG. 7 is a flow chart of the Logarithmic Constrained Inversion Method for inverting the particle size distribution from the scattered light intensity pattern according to the second embodiment.

Calculation of the relative particle size distribution by the Logarithmic Constrained Inversion Method is shown in the flow chart in FIG. 7.

The Logarithmic Constrained Inversion Method is described below in detail.

In this method, Equation (20) is approximated by linear equations. The linear equations are solved under the conditions; (i) $n_r(D)$ is smooth and (ii) $n_r(D)$ is non-negative.

$$\text{Log } I(\theta) = \text{Log } [\int i(D, \theta) n_r(D) dD] \quad (20)$$

First, let's consider Eq. (21), $$I(\theta) = \int_{D_{min}}^{D_{max}} i(D, \theta) n_r(D) dD \quad (21)$$

where $[D_{min}, D_{max}]$ is the droplet size measuring range. When the integral domain $[D_{min}, D_{max}]$ is divided into N small domains $[D_{l-1}, D_l]$ ($l = 1, 2, \ldots N$), Eq. (21) is rewritten as Eq. (22).

$$I(\theta) = \sum_{l=1}^{N} \int_{D_{l-1}}^{D_l} i(D, \theta) n(D) dD \quad (22)$$

If droplet size distribution $n_r(D)$ is constant in $[D_{l-1}, D_l]$ and is replaced by $n_r(D_j)$, Eq. (22) becomes Eq. (23).

$$I(\theta) = \sum_{l=1}^{N} \left( \int_{D_{l-1}}^{D_l} i(D, \theta) dD \right) \cdot n_r(D_l) \quad (23)$$

If the integration in Eq. (23) is expressed as $i_s(D_l, \theta)$, Eq. (23) becomes Eq. (24).

$$I(\theta) + \sum_{l=1}^{N} i_s(D_l, \theta) n_r(D_l) \quad (24)$$

Assuming the measuring angles of $I(\theta)$ are $\theta_1, \theta_2, \ldots \theta_K$, Eq. (24) yields Eq. (25).

$$I(\theta_m) = \sum_{l=1}^{N} i_s(D_l, \theta_m) n_r(D_l) \quad (m = 1, 2, \ldots, K) \quad (25)$$

Equation (25) is also represented as eq. (26).

$$I = G \cdot n_r \quad (26)$$

Where $$I \triangleq \begin{pmatrix} I(\theta_1) \\ I(\theta_2) \\ \vdots \\ I(\theta_K) \end{pmatrix} \quad (27)$$

$$G \triangleq \begin{pmatrix} i_s(D_1,\theta_1) & i_s(D_2,\theta_1) & \ldots & i_s(D_N,\theta_1) \\ i_s(D_1,\theta_2) & i_s(D_2,\theta_2) & \ldots & i_s(D_N,\theta_2) \\ \vdots & & & \vdots \\ i_s(D_1,\theta_K) & i_s(D_2,\theta_K) & \ldots & i_s(D_N,\theta_K) \end{pmatrix} \quad (28)$$

$$n_r \triangleq \begin{pmatrix} n_r(D_1) \\ n_r(D_2) \\ \vdots \\ n_r(D_N) \end{pmatrix} \begin{pmatrix} n_{r1} \\ n_{r2} \\ \vdots \\ n_{rN} \end{pmatrix} \quad (29)$$

In order to obtain the approximate equations for Eq. (20), the transform matrix (Eq. (30)) is multiplied by both sides of Eq. (25) from the left hand side. Then Eq. (31) is obtained $$T \triangleq \begin{pmatrix} \frac{\text{Log } I(\theta_1)}{I(\theta_1)} & 0 & \ldots & 0 \\ 0 & \ddots & & \vdots \\ \vdots & & \ddots & \\ \vdots & & \ddots & 0 \\ 0 & \ldots & 0 & \frac{\text{Log } I(\theta_K)}{I(\theta_K)} \end{pmatrix} \quad (30)$$

$$TI = TGn_r \quad (31)$$

Equation (31) is rewritten as Eq. (32).

$$\overline{I} = \overline{G}n_r \quad (32)$$

The least squares solution of Eq. (32) is obtained by Eq. (33), $$n_r = (\overline{G}^* \overline{G})^{-1} \overline{G}^* \overline{I} \quad (33)$$

where $\overline{G}^*$ represents the transpose matrix of $\overline{G}$. The solution obtained by Eq. (33) is very sensitive to errors in $\overline{I}$. Therefore, the least squares solution under the following conditions (C.1), (C.2) was obtained.

| | |
|---|---|
| $n_r(D)$ is smooth | (C.1) |
| $n_r(D)$ is non-negative | (C.2) |

Concretely speaking, condition (C.1) means that q is kept constant.

$$q = \sum_{j=1}^{N-3} (n_{rj} - 3n_{rj} + 3n_{rj+2} - n_{rj+3})^2 \quad (34)$$

Equation (34) is rewritten as follows, $$q = (Kn_r)^*(Kn_r) = n_r^* K^* K n_r = n_r^* H n_r \quad (35)$$

where $$K \triangleq \begin{pmatrix} 0 & & & & & & \\ 0 & 0 & & & & & \\ 0 & 0 & 0 & & & & \\ 1 & -3 & 3 & -1 & 0 & \ldots & \\ 0 & 1 & -3 & 3 & -1 & 0 & \ldots \\ 0 & 0 & 1 & -3 & 3 & -1 & 0 & \ldots \\ & & & \vdots & & & \\ & & & \vdots & & & \end{pmatrix} \quad (36)$$

$$H \triangleq K^* K. \quad (37)$$

The least squares solution under condition (C.1) is obtained using Lagrange's method of indeterminate coefficients. The solution $n_r$ minimizes Eq. (38).

$$(\overline{G}n_r - \overline{I})^*(\overline{G}n_r - \overline{I}) + \gamma n_r^* H n_r \quad (38)$$

This solution is obtained by Eq. (39).

$$n_r = (\overline{G}^* \overline{G} + \gamma H)^{-1} \overline{G}^* \overline{I} \quad (39)$$

$n_r$ must be non-negative (condition (C.2)).

If $n_r$, obtained by Eq. (39), satisfies the following (Kuhn-Tucker) conditions, $n_r$ is the least squares solution under the conditions (C.1), (C.2).

Conditions $$Y_j \geq 0 \text{ for } j \text{ of } n_{rj} = 0 \quad (40)$$
$$\text{and } Y_j = 0 \text{ for } j \text{ of } n_{rj} > 0 \quad (41)$$

where $y_i$ is an element of y.

$$y = \overline{G}^*(\overline{G}n_r - \overline{I}) + \gamma H n_r \quad (42)$$

$n_r$ is uniquely determined if $(\overline{G}^*\overline{G} + \gamma H)^{-1}$ exists.

Figure 8:
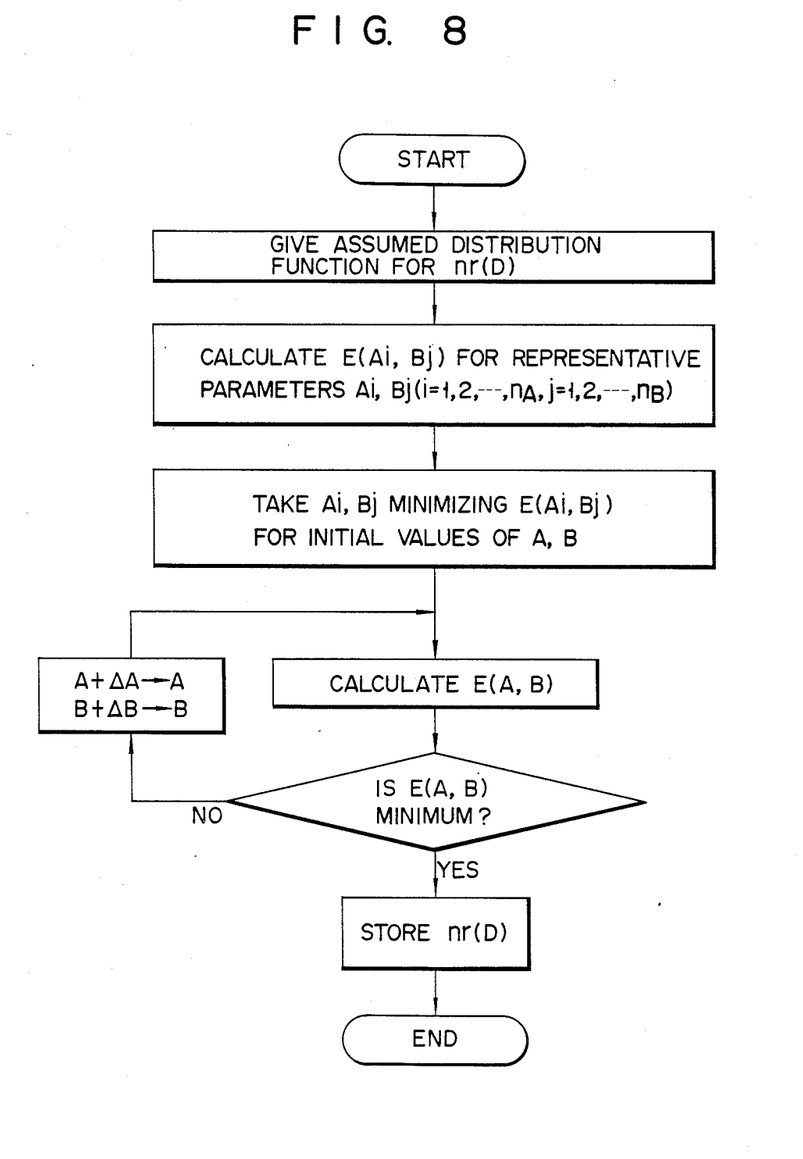
FIG. 8 is a flow chart of the Logarithmic Distribution Function Approximation Method for inverting the particle size distribution from the scattered light intensity pattern according to the second embodiment.

Calculation of the relative particle diameter distribution by the Logarithmic Distribution Function Approximation Method is shown in the flow chart shown in FIG. 8. According to this method, a distribution parameter of $n_r(D)$ is assumed, and a distribution parameter of $n_r(D)$ which minimizes the following equation is determined:

$$E = |\text{Log } [I(\theta)] - \text{Log } [\int i(D,\theta) n_r(D) dD]|^2$$

As the distribution function, a normalized distribution function given by:

$$n_r(D) = (1/\sqrt{2B}) exp |[-(D-A)^2/2B^2]$$

is assumed, and distribution parameters A and B which minimize E are determined.

As described above, in the second embodiment, the absolute particle size distribution can be determined and an application field can be extended. For example, if the absolute value of a particle size distribution can be determined, vapor condition in a turbin can be monitored. Wetness H is given by $W_L/W_B$ where $W_L$ is the weight of a liquid in the vapor and $W_B$ is the total weight of the gas and liquid in the vapor. The pressure in the turbine can be easily measured. When the pressure in the turbine is determined, the density of the gas and the density of the liquid can be determined in accordance with a saturation vapor curve. The number of particles can be determined from the absolute particle size distribution, and the weight $W_L$ of the liquid in the vapor is determined finally. In this manner, it is very useful to be able to obtain the absolute value of the particle size distribution. Note that the present invention is not limited to the particular embodiments described above, and various changes and modifications can be made within the spirit and scope of the present invention.

What is claimed is:

1. A particle size measuring apparatus comprising:
    laser means for outputting a laser beam;
    an optical system for irradiating a number of particles to be measured with a laser beam from said laser means;
    an optical shield, interposed between said optical system and the particles to be measured, for shutting off the light scattered by the optical system;
    detecting means wherein said detecting means comprises optical fibers each having one end positioned at an equal distance from a center of an area containing the particles to be measured and photodetectors connected respectively to the other end of said optical fibers, for measuring a scattered light intensity pattern generated by the particles to be measured irradiated with the laser beam through said optical shield;
    a conversion table for storing conversion coefficients ($T(\theta)$) obtained from a ratio of an absolute value ($I(\theta)$) of the scattered light intensity pattern calculated in accordance with a scattering theory to a measured value ($Ipm(\theta)$) of a scattered light intensity pattern obtained when particles with a known particle diameter and particles density are irradiated with a laser beam said absolute value being expressed in terms of the number of particles whose diameters are within a predetermined range;
    converting means for converting a measured value of the scattered light intensity pattern obtained by irradiating the particles to be measured with the laser beam into the absolute value of the scattered light intensity pattern using the conversion coefficient stored in said conversion table;
    first arithmetic operating means for calculating a relative particle size distribution ($n_r(D)$) of the particles to be measured from the absolute value of the scattered light intensity pattern converted by said converting means said relative particle size distribution being unitless; and
    second arithmetic operating means for calculating an absolute particle size distribution of the particles to be measured from the absolute value of the scattered light intensity pattern obtained from said converting means and the relative particle size distribution obtained from said first arithmetic operating means.

2. An apparatus according to claim 1, wherein said second arithmetic operating means comprises:
    means for calculating a particle density of the particles to be measured from an absolute value of the scattered light intensity pattern of the particles to be measured; and
    means for calculating the absolute particle size distribution by multiplying the particle density with the relative particle size distribution of the particles to be measured.

3. An apparatus according to claim 1, wherein said apparatus further comprises a pair of transparent materials opposed at a predetermined interval for determining an optical path length in a space including particles to be measured.

* * * * *